(12) United States Patent
Polak (10) Patent No.: US 12,186,559 B2
(45) Date of Patent: Jan. 7, 2025

(54) SEMIAUTOMATED ROBOTIC COCHLEAR IMPLANT SURGERY (71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1094 days.

(21) Appl. No.: 16/970,698

(22) PCT Filed: Mar. 20, 2019

(86) PCT No.: PCT/US2019/023075
§ 371 (c)(1),
(2) Date: Aug. 18, 2020

(87) PCT Pub. No.: WO2019/183161
PCT Pub. Date: Sep. 26, 2019

(65) Prior Publication Data
US 2020/0375667 A1 Dec. 3, 2020

Related U.S. Application Data (60) Provisional application No. 62/645,883, filed on Mar. 21, 2018.

(51) Int. Cl.
A61N 1/36 (2006.01)
A61N 1/05 (2006.01)

(52) U.S. Cl.
CPC ....... *A61N 1/36039* (2017.08); *A61N 1/0541* (2013.01)

(58) Field of Classification Search
None
See application file for complete search history.

(56) References Cited

U.S. PATENT DOCUMENTS

2005/0261748 A1 11/2005 van Dijk
2010/0114288 A1 5/2010 Haller et al.
(Continued)

FOREIGN PATENT DOCUMENTS

CN 101801455 A 8/2010
CN 103190966 A 7/2013
(Continued)

OTHER PUBLICATIONS

International Searching Authority/US, International Search Report and Written Opinion of the International Searching Authority, Application No. PCT/US2019/023075, dated Jun. 10, 2019, 18 pages.
(Continued)

*Primary Examiner* — Lynsey C Eiseman
*Assistant Examiner* — James Moss
(74) *Attorney, Agent, or Firm* — Barclay Damon LLP (57) ABSTRACT Arrangements are described for monitoring cochlear implantation surgery. During surgical insertion of a cochlear implant electrode array into a patient cochlea, at least one measurement difference value is determined for at least one electrode contact currently located at a given insertion depth into the patient cochlea based on comparing current stimulus response data for the at least one electrode contact to prior stimulus response data for at least one prior electrode contact previously located at the given insertion depth. A potential trauma response is identified when the at least one measurement difference value exceeds a defined difference value.

16 Claims, 6 Drawing Sheets (56) References Cited

U.S. PATENT DOCUMENTS

| | | | |
|---|---|---|---|
| 2011/0098719 | A1 | 4/2011 | Llinas et al. |
| 2015/0088225 | A1 | 3/2015 | Noble et al. |
| 2018/0050196 | A1* | 2/2018 | Pawsey ............... A61B 34/30 |
| 2018/0056058 | A1* | 3/2018 | Heasman ........... A61N 1/36036 |
| 2019/0030323 | A1* | 1/2019 | Koka ................. A61N 1/0541 |

FOREIGN PATENT DOCUMENTS

| | | |
|---|---|---|
| CN | 103347465 A | 10/2016 |
| CN | 106232175 A | 12/2016 |
| CN | 106794344 A | 5/2017 |
| WO | WO 02/32498 A1 | 4/2002 |
| WO | WO 2017/048342 A1 | 3/2017 |
| WO | WO 2017//131675 A1 | 8/2017 |

OTHER PUBLICATIONS

European Patent Office, Extended European Search Report, Application No. 19771122.9. dated Nov. 26, 2021, 8 pages.

China National Intellectual Property Administration, Office Action, Application No. 201980019175.8, dated Feb. 28, 2023, 6 pages (in Chinese).

Second Office Action in Chinese Application No. 201980019175.8 dated Sep. 13, 2023, 13 pages (including machine translation, 17 pages).

\* cited by examiner

SEMIAUTOMATED ROBOTIC COCHLEAR IMPLANT SURGERY

This application claims priority from U.S. Provisional Patent Application 62/645,883, filed Mar. 21, 2018, which is incorporated herein by reference in its entirety.

TECHNICAL FIELD

The present invention relates to cochlear implants, and more particularly, to a real time system and methodology for detecting trauma created by surgical insertion of an electrode array into the cochlea.

BACKGROUND ART

Figure 1:
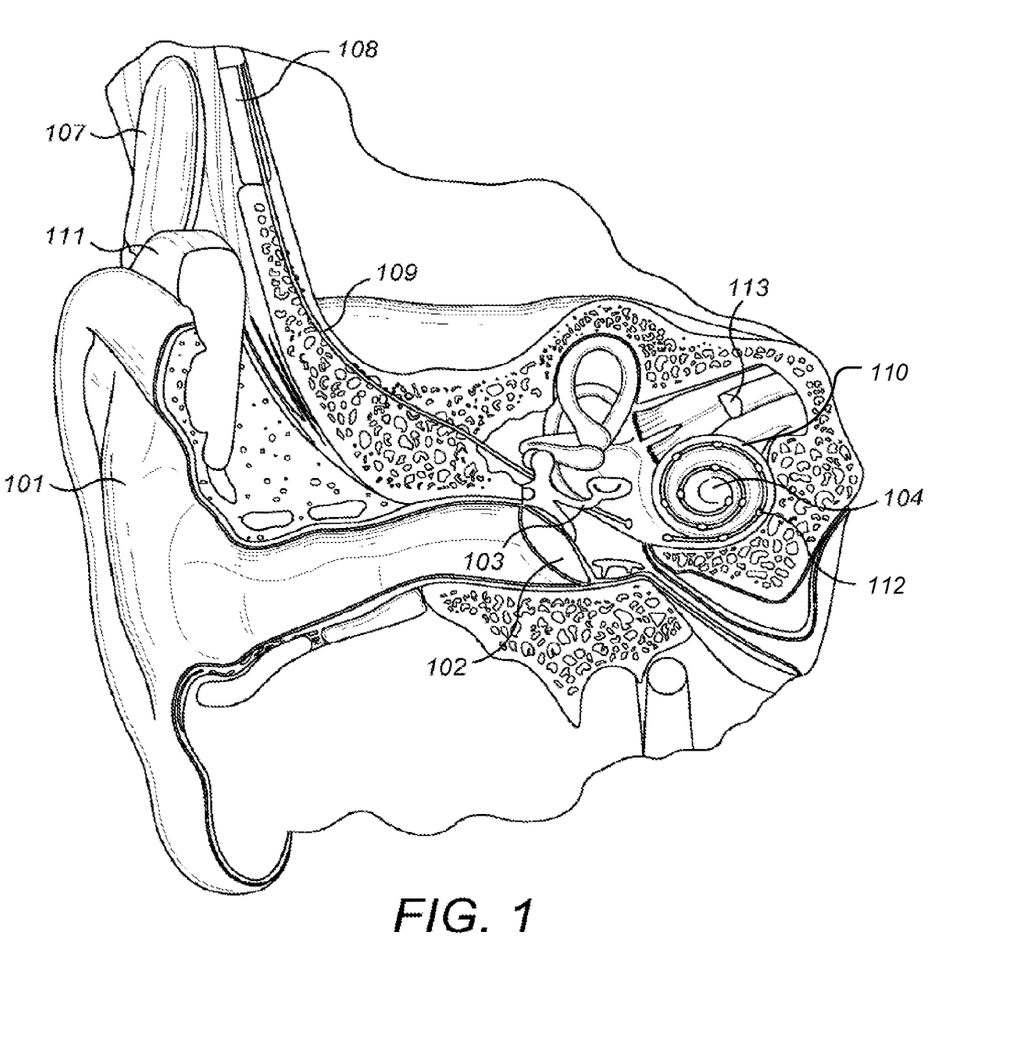
FIG. 1 shows structures in a human ear having a cochlear implant system.

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission by an external transmitter coil 107 into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an electrode array 110 inserted into the cochlea. Typically, this electrode array 110 includes multiple electrode contacts on its surface that provide selective stimulation of the cochlea 104. Stimulation is either carried out against an external reference electrode contact (i.e., a remote ground contact) outside the cochlea or against another electrode contact of the array within the cochlea 104.

The insertion of the electrode array 110 requires surgery. Cochlear implant manufacturers offer to surgeons a wide range of mechanical tools necessary for implantation of the device. However, since the electrode array 110 is inserted into the cochlea 104 through a small hole, the surgeon gets no visual conformation of the exact placement of the electrode array 110 within the cochlea 104 itself. Insertion depth may be estimated by the part of the electrode array 110 that has not yet been inserted into the cochlea 104 but apart from that, the exact location of already inserted contacts is unknown during surgery.

It is important to minimize trauma to the delicate tissues and structures of the cochlea during implantation of the electrode array. This can be determined by measuring hearing preservation. If hearing is preserved, that guarantees minimal structural trauma has occurred. Measurement of hearing preservation is possible in near-to-real time by measurement of intracochlear evoked potentials in response to acoustic or mechanical stimuli. The evoked potentials are recordable via the implanted electrode contacts in a large group of patients with low frequency hearing, with the most sensitive frequency for this type of measurement being 500-1000 Hz.

SUMMARY

Embodiments of the present invention are directed to a surgical insertion system for controlling cochlear implantation surgery. An insertion tool is configured for inserting an electrode array into a patient cochlea, wherein the electrode array includes a plurality of electrode contacts distributed along an outer surface. An insertion controller is configured to control the inserting of the electrode array by the insertion tool and has at least one hardware processor executing program instructions for: (1) determining at least one measurement difference value for at least one electrode contact currently located at a given insertion depth into the patient cochlea based on comparing current stimulus response data for the at least one electrode contact to prior stimulus response data for at least one prior electrode contact previously located at the given insertion depth, (2) identifying a potential trauma response when the at least one measurement difference value exceeds a defined difference value, and (3) pausing the surgical insertion when the potential trauma response is identified.

In further specific embodiments, the insertion controller program instructions further comprise redetermining the at least one measurement difference value at least one time during a pause period, and resuming the surgical insertion when the at least one measurement difference value no longer exceeds the defined difference value. The insertion controller program instructions also may further comprise partially withdrawing the electrode array from patient cochlea and/or partial rotating the electrode array within the patient cochlea during the pause period. The insertion controller program instructions may redetermine the at least one measurement difference value a plurality of times until the at least one measurement difference value no longer exceeds the defined difference value.

In specific embodiments, the insertion controller program instructions may determine a plurality of measurement difference values for a plurality of electrode contacts currently located at a plurality of given insertion depths and identify a potential trauma response when any of the measurement difference values exceeds the defined difference value. In addition or alternatively, the insertion controller program instructions may determine the at least one measurement difference value based on comparing current stimulus response data to prior stimulus response data for a plurality electrode contacts previously located at the given insertion depth.

Embodiments of the present invention also include a computer-implemented method employing at least one hardware implemented computer processor for monitoring cochlear implantation surgery. During surgical insertion into a patient cochlea of a cochlear implant electrode array, the at least one hardware processor is operated to execute program instructions for: (1) determining at least one measurement difference value for at least one electrode contact currently located at a given insertion depth into the patient cochlea based on comparing current stimulus response data for the at least one electrode contact to prior stimulus response data for at least one prior electrode contact previously located at the given insertion depth, and (2) identifying a potential trauma response when the at least one measurement difference value exceeds a defined difference value.

In further specific embodiments, the executed program instructions may further comprise pausing and/or slight withdrawal, usually 1 mm (to come to the point where the recordings did not indicate any trauma, the surgical insertion when the potential trauma response is identified, redetermining the at least one measurement difference value at least one time during a pause period, and resuming the surgical insertion when the at least one measurement difference value no longer exceeds the defined difference value. The executed program instructions may further comprise partially withdrawing the cochlear implant electrode array from patient cochlea and/or partially rotating the electrode array within the patient cochlea during the pause period.

The executed program instructions may redetermine the at least one measurement difference value a plurality of times until the at least one measurement difference value no longer exceeds the defined difference value. The executed program instructions may determine a plurality of measurement difference values for a plurality of electrode contacts currently located at a plurality of given insertion depths and identify a potential trauma response when any of the measurement difference values exceeds the defined difference value. In addition or alternatively, the executed program instructions may determine the at least one measurement difference value based on comparing current stimulus response data to prior stimulus response data for a plurality electrode contacts previously located at the given insertion depth.

DETAILED DESCRIPTION

There are several hearing loss causing mechanisms that can occur during the electrode insertion into the patient's cochlea. Most of these mechanisms can be avoided or reversed by controlling the force and speed of the insertion and timely maneuvering of the electrode during the insertion. Thus embodiments of the present invention are directed to arrangements to create an automated system for controlling cochlear implantation surgery to navigate the surgeon during insertion of the electrode array into the cochlea. In real time or near real time while the array is being inserted, at least one measurement difference value is determined for at least one electrode contact that is currently located at a given insertion depth into the patient cochlea, based on comparing current stimulus response data for the at least one electrode contact to prior stimulus response data for at least one prior electrode contact that was previously located at the given insertion depth. A potential trauma response is then identified when the at least one measurement difference value exceeds a defined difference value, and the surgical insertion is then paused.

Figure 2:
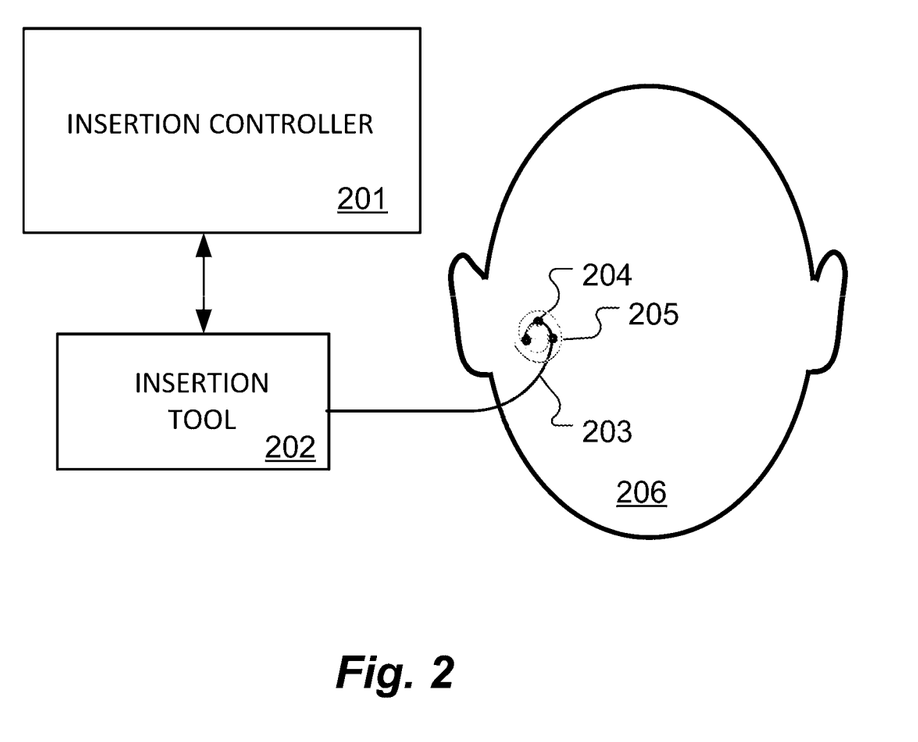
FIG. 2 shows various functional blocks in a system for surgical insertion of a cochlear implant electrode array according to an embodiment of the present invention.
Figure 3A:
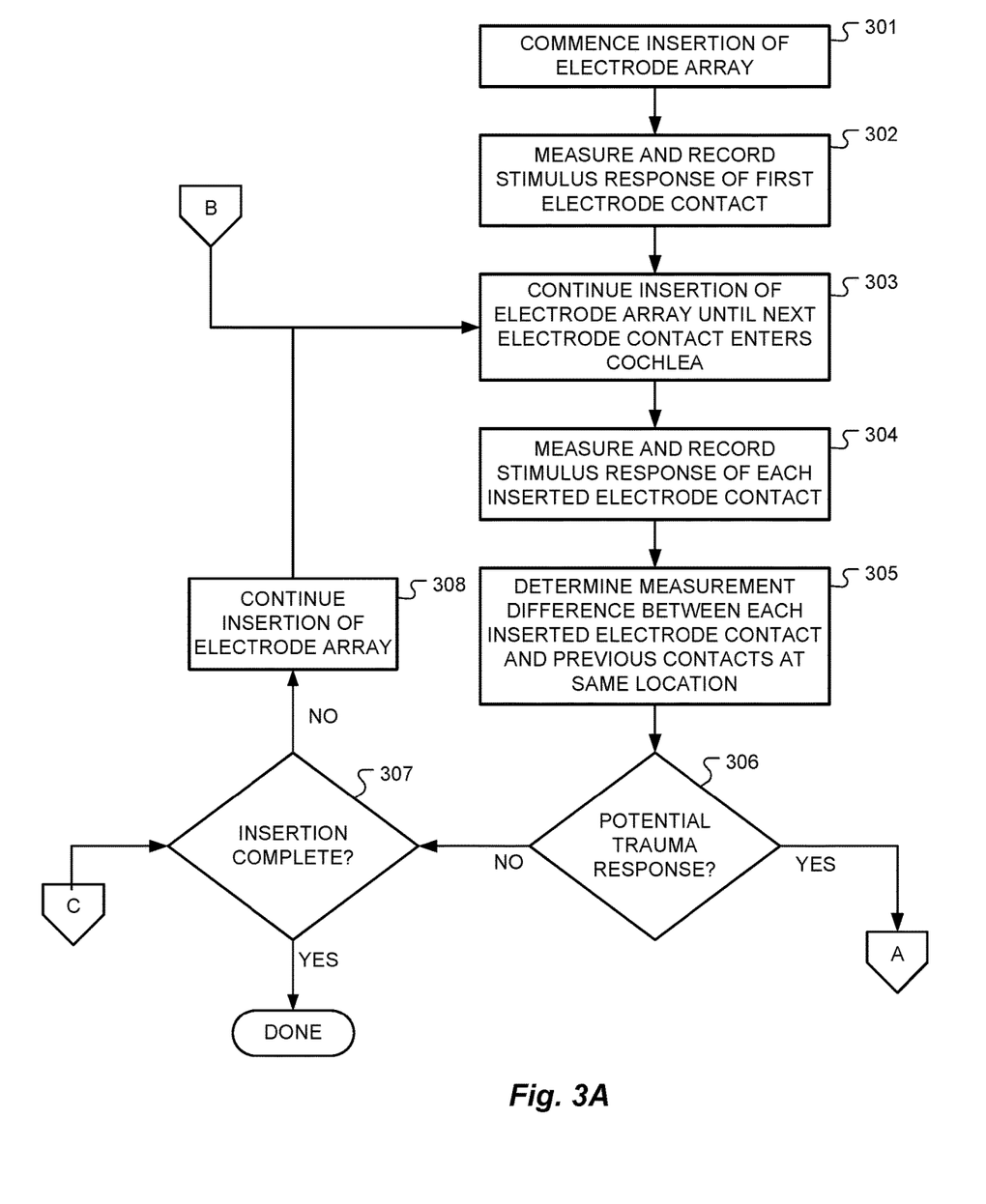
FIGS. 3A-3B show various logical steps in surgical insertion of a cochlear implant electrode array according to an embodiment of the present invention.
Figure 3B:
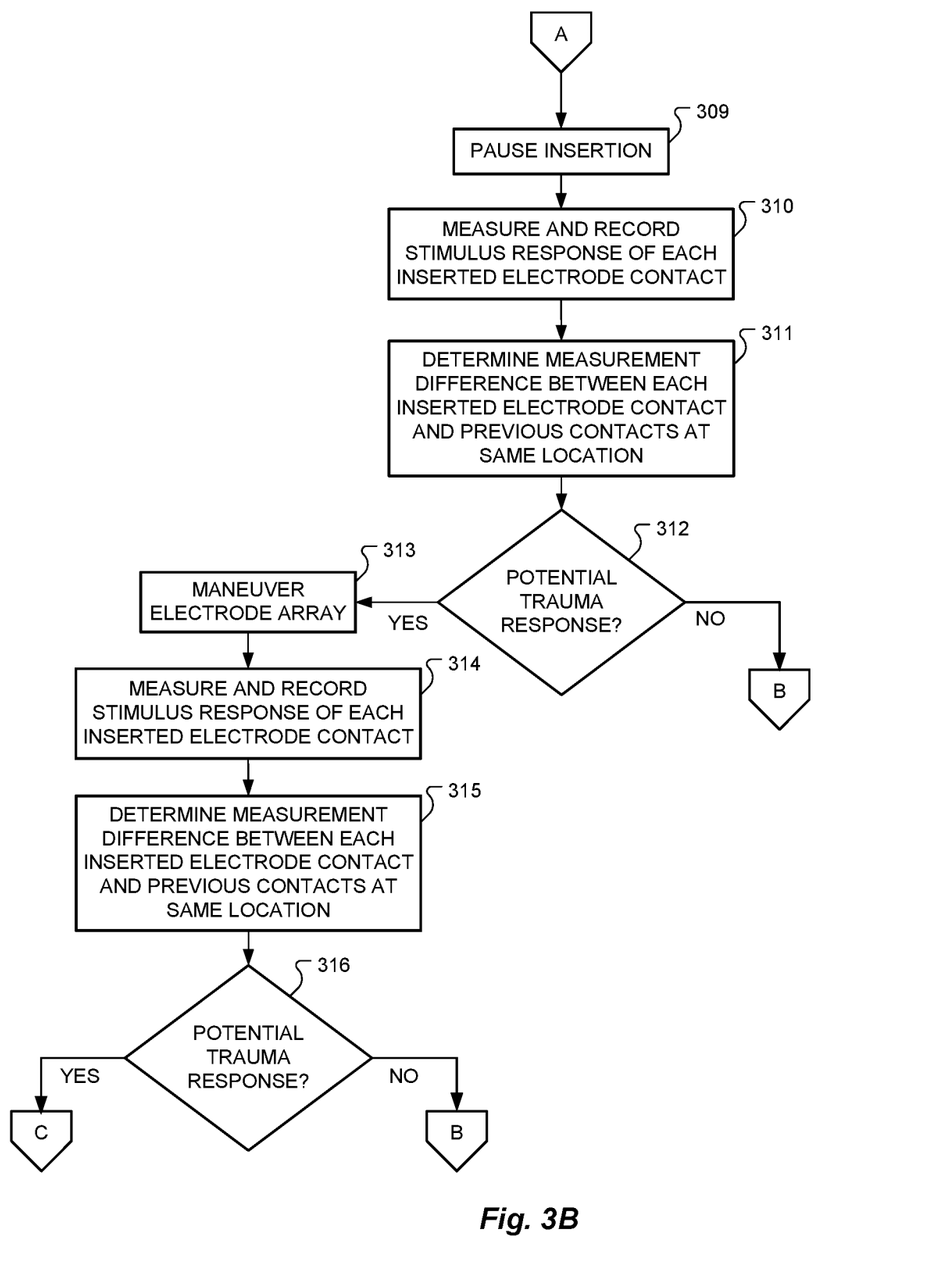

FIG. 2 shows various functional blocks in a system and FIGS. 3A-3B show various logical steps in a corresponding method of surgical insertion of a cochlear implant electrode array according to an embodiment of the present invention. An insertion tool 202 is configured for inserting an electrode array 203 with multiple electrode contacts 204 distributed along its outer surface into a cochlea 205 of an implanted patient 206. An insertion controller 201 includes at least one hardware implanted processor device which is controlled by software instructions to control the insertion process by instructing the insertion tool 202 to control the inserting of the electrode array 203. The program instructions that are executed by the insertion controller 201 include program instructions to commence insertion of the electrode array 301.

Figure 4A:
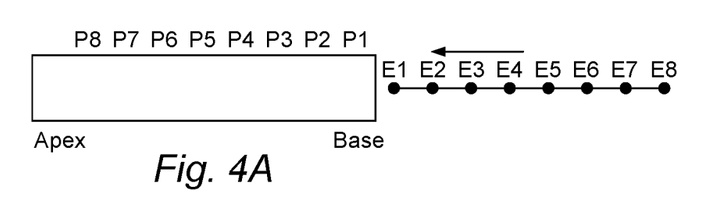
FIGS. 4A-4F illustrate the progression of inserting an electrode array according to an embodiment of the present invention.
Figure 4B:
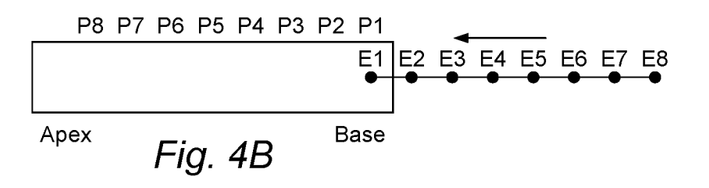
Figure 4C:
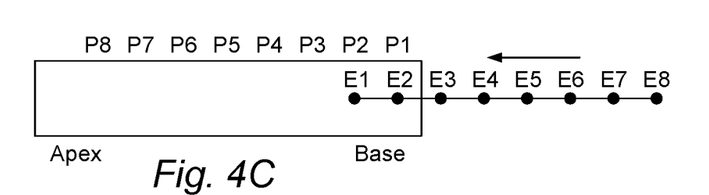

As the electrode array 203 starts to enter the cochlea 205, FIG. 4A, once the first electrode contact E1 enters into the cochlea 205 and valid impedance is present on that contact, FIG. 4B, the stimulus response is measured and recorded for that contact at that location, step 302. The insertion controller 201 controls the insertion tool 202 to continue insertion of the electrode array 203 into the cochlea 205 until the next contact E2 enters, step 303, FIG. 4C. The stimulus response is measured and recorded for each inserted contact at its current location, step 304.

The stimulus response measurements and recordings may include, for example, parameters such as response latencies, amplitudes and/or frequencies and phases of the evoked response signals, which may be recorded and evaluated continuously (with the electrode array being inserted at a controlled speed) or step-wise where the electrode array 203 is inserted into the cochlea 205 in steps and after each stopping the response measurement and recording is performed. The stimulus response signal amplitudes should be greater than the noise floor. For example, the amplitude of the stimulus response signals typically may vary from approximately 0.2 uV up to 800 uV recorded over a period up 8 sec. Typical recording time is 5-8 sec. Generally, the larger the signal, the smaller the recording period. Response measurement and record can be successfully performed even in patients with relatively poor hearing, even with low frequency thresholds at around 100 dB of hearing loss.

At least one measurement difference value is then determined, step 305, for at least one electrode contact 204 that is currently located at a given insertion depth into the patient cochlea 205 based on comparing current stimulus response data for the at least one electrode contact to prior stimulus response data for at least one prior electrode contact previously located at the given insertion depth. Basically, difference values might typically be determined for each electrode contact for which there were one or more other electrode contacts previously at the same location.

Figure 4D:
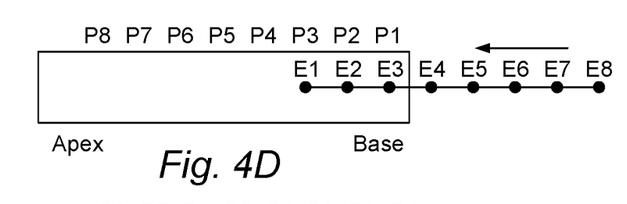
Figure 4E:
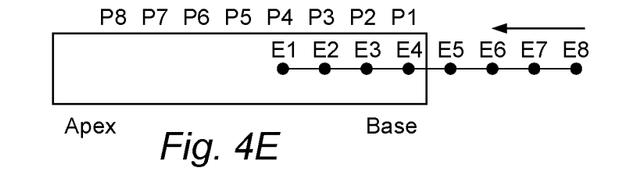
Figure 4F:
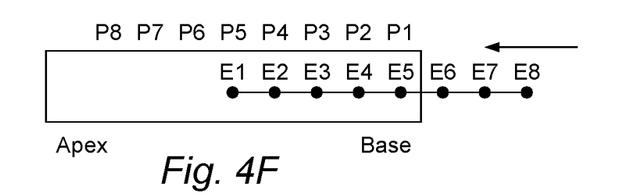

More specifically, when the electrode array 203 has been inserted up to the point of two of the electrode contacts E1 and E2 being within the cochlea 205 (FIG. 4C), response measurement recordings from the second electrode contact E2 when it was just inserted are compared with the recordings from the first electrode contact E1 at the time when it was just introduced into the cochlea 205. Then when the electrode array 203 is inserted up to the point of three electrode contacts E1, E2 and E3 being within the cochlea 205 (FIG. 4D), then response measurement recordings from the third electrode contact E3 after it was just inserted are compared with the recordings from the second electrode contact E2 when it was just inserted and from the first electrode contact E1 when it was just inserted. At the same time, the response measurement recordings from the second electrode contact E2 at its current location are compared to the response measurement recordings from the first electrode contact E1 when it was at the same location. And so on.

When at least one measurement difference value exceeds a defined difference value threshold, step 306, then a potential trauma response is identified and the insertion is paused, step 309. In specific embodiments, the insertion controller 201 program instructions may determine multiple measurement difference values for multiple different electrode contacts 204 currently located at various different given insertion depths within the cochlea 205, and then identify a potential trauma response when any of the measurement difference values exceeds the defined difference value. When at least one measurement difference value does not exceed the defined difference value threshold at step 306, then, if the insertion is complete, step 307, and stops. Otherwise, if the insertion is not complete at step 307, insertion of the electrode array 203 continues until the next contact 204 enters the cochlea 205, repeating from step 303.

Figure 5:
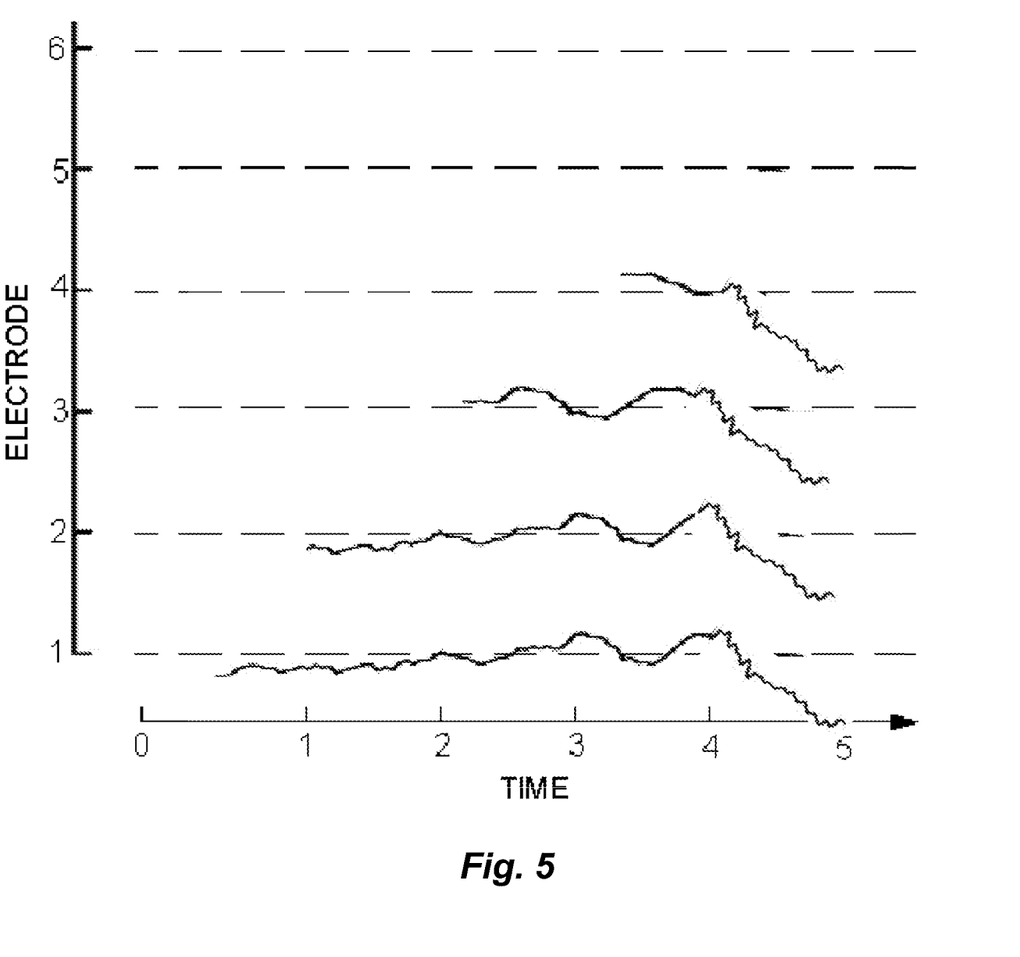
FIG. 5 shows the revoked responses of a sequence of electrode arrays during surgical insertion.

For example, FIG. 5 shows examples of response signal measurements recorded at the advancing electrode contacts 204 over time. Usually the signal amplitude tends to generally increase up to some inflection point, after which it generally decreases until insertion of the electrode array 203 is completed. This depends on the specific stimulus frequency that is used. Such expected signal behaviour would be indicative of no potential trauma and no hearing loss. However, potential trauma and hearing loss may be observed when the amplitudes of the evoked response signals decrease at a given location in the cochlea 205. In the examples shown in FIG. 5, this can be seen in the signals beginning at time 4 where the signal amplitudes are uniformly lower at all the measurement locations by up to 30%. At this stage of electrode insertion, the surgeon is needed to be notified of the potential trauma.

After pausing the insertion at step 309 for a short period because of a potential trauma, then it may be useful to proceed as shown in FIG. 3B by measuring and recording the stimulus response again for each inserted contact 204 at its current location, step 310, and then determining measurement difference values between each inserted electrode contact 204 for which there are response measurements of a previous electrode contact 204 to occupy the same location, step 311, and then determining again if a potential trauma response is identified, step 312. It may be that the response measurements return to normal values after pausing, in which case, the insertion of the electrode array 203 again continues until the next contact 204 enters the cochlea 205, repeating from step 303.

If a potential trauma response is still present at step 312, then the surgeon may take steps to try to resolve the problem; for example, maneuvering the array 203, step 313, for example, by partially rotating the array 203 and/or partially withdrawing the array 203. Then the stimulus response is measured and recorded again for each inserted contact 204 at its current location, step 314, and the measurement difference values are determined between each inserted electrode contact 204 for which there are response measurements of a previous electrode contact 204 to occupy the same location, step 315, and then determining again if a potential trauma response is identified, step 316. If the response measurements return to normal values (no potential trauma identified) after maneuvering the electrode array 203, then the insertion of the electrode array 203 again continues until the next contact 204 enters the cochlea 205, repeating from step 303. If there still is a potential trauma present at step 316 after maneuvering the electrode array 203, then the process ends (insertion complete, step 307) and the surgeon decides whether to withdraw the array without completing the surgery or to complete the insertion procedure notwithstanding the trauma that is created.

The program instructions executed by the insertion controller 201 may be configured to propose which part of the electrode array 203 creates the greatest portion of the insertion force. Then the electrode array can be maneuvered to lower this insertion force as much as possible.

For example, if the amplitude of stimulus response recordings dramatically increases during the insertion at a specific location in the cochlea 205, this may suggest that the electrode array is pressing on the basilar membrane or is too close to the inner ear hair cells and related neural structures. Often in such cases the latencies of stimulus responses gets shorter while at the other parts of the cochlea 205, the amplitudes of the stimulus responses may actually be lower or remain unchanged. This may suggest that such electrode contacts 204 are on the lateral wall of the scala tympani and thus potentially causing the increase of insertion electrode forces. In such cases it is advised to stop the insertion, wait, and possibly slightly withdraw the electrode array 203 by some small portion (e.g., 1 mm or more). The surgeon may then continue with the insertion rotating the electrode array to navigate the trajectory of the electrode array tip, depending on the type of electrode array 203.

The evaluating values could be the amplitude of the recording signal. It can be amplitude defined as peak-to-peak amplitude (difference between the global/local maximum and global/local minimum) or the amplitudes related specific stimulating frequency, i.e. if the stimulating signal consists of one frequency, i.e. tone pip of frequency f the evaluated amplitude would be related to frequency f. Another value to evaluate are latencies of the recorded signals. Frequency analysis of the stimulus response signals may be performed to determine what types of responses are being recorded. Here, the signal is represented by phase and amplitude at each particular frequencies of recorded signal. The possible specific stimulus responses may include cochlear microphonics (CM), summating potentials (SM), and/or compound action potentials (CAP). For example, CM amplitude for an electrode array may increase by up to ten times when a given electrode contact is moved from the lateral wall to the vicinity of the basilar membrane closer to the hair cells while still maintaining depth position in the scala tympani without causing any additional hearing loss. In such a case, the latency of the stimulus response often shortens.

Changes in the stimulus responses can be reversible and can be controlled by the insertion force and speed, withdrawing, and rotating the electrode array. For example, optimal insertion forces to preserve residual hearing should be maintained less than 25 mN and should never exceed 40 mN. Other influencing factors for hearing preservation include the geometry of the electrode opening into the cochlea and prevention of blood and bone dust in the cochlea.

The risk of hearing trauma increases with insertion depth into the cochlea. Any potential trauma identified during insertion of the electrode array should be immediately evaluated. One advantage of embodiments of the present invention is that the deeper the electrode array is inserted into the cochlea, the more precisely it can be controlled. As an additional benefit, the insertion depth of the electrode array can be estimated. This also provides a way to evaluate and compare the specific insertion behaviour of various different electrode arrays Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components. Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A surgical insertion system for identifying a trauma response, the system comprising:
    an insertion tool configured for inserting an electrode array into a patient cochlea, wherein the electrode array includes a plurality of electrode contacts distributed along an outer surface, the plurality electrode contacts including at least one first electrode contact and at least one electrode contact; and
    an insertion controller, configured to control the inserting of the electrode array by the insertion tool, including at least one hardware processor executing program instructions for:
        determining at least one measurement difference value for the at least one first electrode contact located at a given insertion depth into the patient cochlea during insertion of the electrode array based on comparing stimulus response data for the at least one first electrode contact at the given insertion depth to stimulus response data for the at least one second electrode contact when the at least one second electrode contact was located at the given insertion depth during the insertion of the electrode array, and
        identifying a potential trauma response when the at least one measurement difference value exceeds a defined difference value.

2. The system according to claim 1, wherein the insertion controller program instructions further comprise:
    redetermining the at least one measurement difference value at least one time during a pause period when the at least one measurement difference value no longer exceeds the defined difference value.

3. The system according to claim 2, wherein the insertion controller program instructions further comprise:
    partially withdrawing the cochlear implant electrode array from patient cochlea during the pause period.

4. The system according to claim 2, wherein the insertion controller program instructions further comprise:
    partially rotating the cochlear implant electrode array within patient cochlea during the pause period.

5. The system according to claim 2, wherein the insertion controller program instructions redetermine the at least one measurement difference value a plurality of times until the at least one measurement difference value no longer exceeds the defined difference value.

6. The system according to claim 1, wherein the insertion controller program instructions determine a plurality of measurement difference values for a plurality of the electrode contacts located at a plurality of given insertion depths and identify a potential trauma response when any of the measurement difference values exceeds the defined difference value.

7. The system according to claim 1, wherein the plurality of electrode contacts further includes at least one e contact and wherein the insertion controller program instructions further comprise determining the at least one measurement difference value based on comparing stimulus response data for the at least one first electrode contact at the given insertion depth to stimulus response data for the at least one third electrode contact when the at least one third electrode contact was located at the given insertion depth during the insertion of the electrode array.

8. A computer-implemented method employing at least one hardware implemented computer processor for identifying a trauma response during insertion of an electrode array into a patient cochlea, the elect rode array including a of electrode contacts distributed along a n outer surface, the plurality of electrode contacts including at least one first electrode contact and at least one second electrode contact, the method comprising:
    operating the at least one hardware processor to execute program instructions for:

determining at least one measurement difference value for the at least one first electrode contact located at a given insertion depth into the patient cochlea during the insertion of electrode array based on comparing stimulus response data for the at least one first electrode contact at the given insertion depth to stimulus response data for the at least one second electrode contact when the at least one second electrode contact was located at the given insertion depth during the insertion of the electrode array, and identifying a potential trauma response when the at least one measurement difference value exceeds a defined difference value.

9. The method according to claim 8, wherein the executed program instructions further comprise:

redetermining the at least one measurement difference value at least one time during a pause period when the at least one measurement difference value no longer exceeds the defined difference value.

10. The method according to claim 9, wherein the executed program instructions further comprise:

partially withdrawing the cochlear implant electrode array from the patient cochlea during the pause period.

11. The method according to claim 9, wherein the insertion controller program instructions further comprise:

partially rotating the cochlear implant electrode array within the patient cochlea during the pause period.

12. The method according to claim 9, wherein the executed program instructions redetermine the at least one measurement difference value a plurality of times until the at least one measurement difference value no longer exceeds the defined difference value.

13. The method according to claim 8, wherein the executed program instructions determine a plurality of measurement difference values for a plurality of the electrode contacts located at a plurality of given insertion depths and identify the potential trauma response when any of the measurement difference values exceeds the defined difference value.

14. The method according to claim 8, wherein the plurality of electrode contacts further includes at least one third electrode contact and wherein the executed program instructions determine the at least one measurement difference value based on comparing the stimulus response data for the at least one first electrode contact at the given insertion depth to stimulus response data for the at least one third electrode contact when the at least one third electrode contact was located at the given insertion depth during the insertion of the electrode array.

15. The system according to claim 1, wherein the insertion controller program instructions further comprise:

pausing the surgical insertion when the potential trauma response is identified.

16. The method according to claim 8, wherein the executed program instructions further comprise:

pausing the surgical insertion when the potential trauma response is identified.

* * * * *